United States Patent
Hagen et al.

(10) Patent No.: US 6,300,761 B1
(45) Date of Patent: Oct. 9, 2001

(54) ANTENNA ARRAY FOR MAGNETIC RESONANCE EXAMINATIONS

(75) Inventors: Juergen Hagen, Erlangen; Ludwig Kreischer, Dormitz; Arne Reykowski, Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/450,294

(22) Filed: Nov. 29, 1999

(30) Foreign Application Priority Data

Nov. 27, 1998 (DE) .............................................. 198 54 924

(51) Int. Cl.⁷ .................................................... G01V 3/00
(52) U.S. Cl. ........................................... 324/318; 600/421
(58) Field of Search ..................... 324/318, 322, 324/300, 306, 307, 309, 314; 600/421, 422

(56) References Cited

U.S. PATENT DOCUMENTS

| 5,389,880 | 2/1995 | Mori . |
| 5,430,378 | 7/1995 | Jones . |
| 5,548,218 | 8/1996 | Lu . |
| 5,594,337 | 1/1997 | Boskamp . |
| 5,708,361 | 1/1998 | Wang et al. . |
| 5,951,474 | * 9/1999 | Matsunaga et al. ................. 324/322 |
| 6,137,291 | * 10/2000 | Szumowski et al. ................ 324/318 |

FOREIGN PATENT DOCUMENTS

| 195 32 137 | 4/1996 | (DE) . |
| WO89/05115 | 6/1989 | (WO) . |

OTHER PUBLICATIONS

"Twelve Antenna Element Lower Extremities/Pelvic Array for MRI(A)," Jones et al., Proc. ISMRM, 6$^{th}$ Meeting, May, 1998, p. 440.

"Lower Extremities: MR Angiography with a Unilateral Telescopic Phase–Array Coil," Kojima et al., Radiology, vol. 196, No. 3 (1995), pp. 871–875.

* cited by examiner

Primary Examiner—Louis Arana
(74) Attorney, Agent, or Firm—Schiff Hardin & Waite

(57) ABSTRACT

An antenna array for magnetic resonance examinations has array elements that are decoupled from each other and that are independent, the array elements being arranged in two adjacent rows. Each array elements is formed by two antenna elements whose respective sensitivity axes reside perpendicular to one another.

13 Claims, 4 Drawing Sheets

ANTENNA ARRAY FOR MAGNETIC RESONANCE EXAMINATIONS

BACKGROUND OF THE INVENTION

1. Field of the Invention

The present invention is directed to an antenna array for magnetic resonance examinations of the type having array elements that are decoupled from each other and are independent, and which are arranged in two adjacent rows.

2. Description of the Prior Art

An antenna array of this type is described in an article by R. Jones with the title "Twelve Antenna Element Lower Extremity/Pelvic Array for MRI (A)", published in the conference volume for the ISMRM 1998 on page 440, "Proceedings of the International Society for Magnetic Resonance in Medicine, $6^{th}$ Scientific Meeting and Exhibition, May 1998, Sidney, Australia." The antenna array is fashioned as a bilateral extremity array for the examination of the entire vessel system below the aorta bifurcation. In two rows, four saddle coil pairs are adjacently arranged with one coil per pair per row, which cover the normal length of the lower extremities of an adult. For decoupling, apart from a strictly symmetrical construction of the two rows, the saddle coil pairs of one row are arranged so as to be rotated 90° relative to the other row.

The article by K. Y. Koyima et al.: "Lower Extremities: MR Angiography with a Unilateral Telescopic Phased-Array Coil" published in Radiology, vol. 196, No. 3, page 871 through 875, 1995 describes a unilateral telescopic phased-array-antenna with six saddle coils, which are sensitive to a linearly polarized field vector. The upper saddle coils are fashioned larger than the lower ones in order to achieve a good filling factor.

Not only the bilateral antenna array but also the unilateral antenna array has array elements with a linear antenna characteristic; this means that the primary sensitivity direction of the array elements extends along one single axis.

U.S. Pat. No. 5,430,378 discloses an antenna array with circularly polarizing array elements. Each array element is formed by two ring coils that are oriented perpendicularly to one another, whereby one ring coil is mounted in a base plate and the other ring coil is mounted on a carrier that is perpendicularly and symmetrically arranged relative to the base plate. The antenna array is fashioned for the examination of the lower extremities, the sensitivity area of the two ring coils of the individual antenna elements covering both extremities. Coupling ensues by a strictly symmetrical arrangement of the ring coils and by a partial overlap of neighboring ring coils.

The antenna array described in U.S. Pat. No. 5,548,218 also has circularly polarizing array elements that are fashioned for MR examinations of the lower extremities. Each array elements is formed by a ring coil and a butterfly coil. The middle area of the array elements is installed in a patient bed, whereas the outer areas are flexibly fashioned. This allows the outer elements to be "unfolded" away in order to position the patient. After the positioning, the outer areas are put on the patient, so that the entire lower extremities can be imagined with a high filling factor of the antenna. Here, the sensitivity area of the circularly polarizing array elements also encompassed both extremities.

The antenna array described in the U.S. Pat. No. 5,594, 337 also has array elements whose sensitivity area encompasses both extremities.

Two decoupling modes are described in PCT Application WO 89/05115. The first mode is to arrange neighboring antenna elements in a partially overlapping manner. The second one transforms the input impedance of a connected pre-amplifier in a high-resistance manner.

U.S. Pat. No. 5,708,361 describes a way to decouple neighboring antenna elements, which does not require a specific geometrical arrangement of the array elements to be decoupled. The conductors of the array elements to be decoupled have an interruption (gap), and are connected in parallel to one another. The interruptions are short-circuited with at least one capacitor, with the decoupling being effected by a selection of the capacitance.

The antenna arrays described above enable a continuous display of the blood vessels in the lower extremities without repositioning the patient relative to the array. In comparison to the imaging of the blood vessels with a whole body resonator, a higher signal quality is therewith achieved. It is still desirable, however, to further increase the signal quality and therewith the signal-to-noise ratio in order to be able to also image finer blood vessels.

SUMMARY OF THE INVENTION

An object of the present invention is to provide an antenna array that has an improved signal-to-noise ratio for the examination of the lower extremities.

This object is achieved in an antenna array having array elements each formed by two antenna elements whose respective sensitivity axes reside perpendicular to one another. During the application, only one leg is situated in the sensitivity area of each array element, as a result of which noise produced the leg that is not being examined at that moment can no longer superimpose on the useful signal. In addition, each array element has a circularly polarized antenna characteristic, as a result of which the signal-to-noise ratio is further improved.

Coupling of the antenna elements of the first row, which neighbor the antenna elements of the second row, are suppressed by a decoupling circuit. The decoupling circuit is connected to the neighboring antenna elements to be decoupled. Therewith, by means of magnetic resonance imaging, a continuous display of the blood vessels in the lower extremities with a high signal-to-noise ratio is obtained without having to reposition the patient relative to the array.

In an embodiment, neighboring parts of the array elements of the two rows are fastened by a bar that is arranged between the rows. With the patient in a recumbent position, the bar is placed upon the patient bed between the legs. The antenna elements of the two rows that are opposite to one another thereby remain in a fixed spacial position relative to one another. The coupling of the two antenna elements that is determined by the geometrical arrangement is compensated by the decoupling circuit. Proceeding away from the bar, the individual array elements are curved, so that they are shaped in a U-shaped manner in a plane perpendicular to the direction of the magnetic basic field of the magnetic imaging apparatus and so that they cover the legs.

In a further embodiment, the parts of the array elements projecting from the bar in the transverse direction are flexibly fashioned. The two rows of array elements thus can be adapted to examination areas of different sizes.

Given examination of the lower extremities, a particularly high filling factor results in further embodiment, wherein a first group of the array elements is more strongly curved and surrounds a smaller examination space than a second group of the array elements. Therewith, the antenna array is well-adapted to the different dimensions of thigh and lower leg.

In another embodiment the array elements form a part of a cover or "hood", that is open at the bottom, for a patient bed. Due to the construction that is open at the bottom, the antenna array can be combined with many support aids for pressure-free support of knees and heels. In contrast to known antenna arrays, the imaging of a moderately angled leg supported in the knee is also possible. Many times, patients with an advanced occlusive disease of the lower extremities can only stretch the legs fully with difficulty and need careful support in order to minimize the danger of pain and therewith motion artefacts during the magnetic resonance examination.

In further embodiment, a pre-amplifier that is arranged in the middle bar is connected to the respective antenna elements. Particularly short signal lines to the pre-amplifier result. This allows the pre-amplifier input impedance to be matched to the antenna elements in an almost ideally high-resistance manner.

DESCRIPTION OF THE PREFERRED EMBODIMENTS

Figure 1:
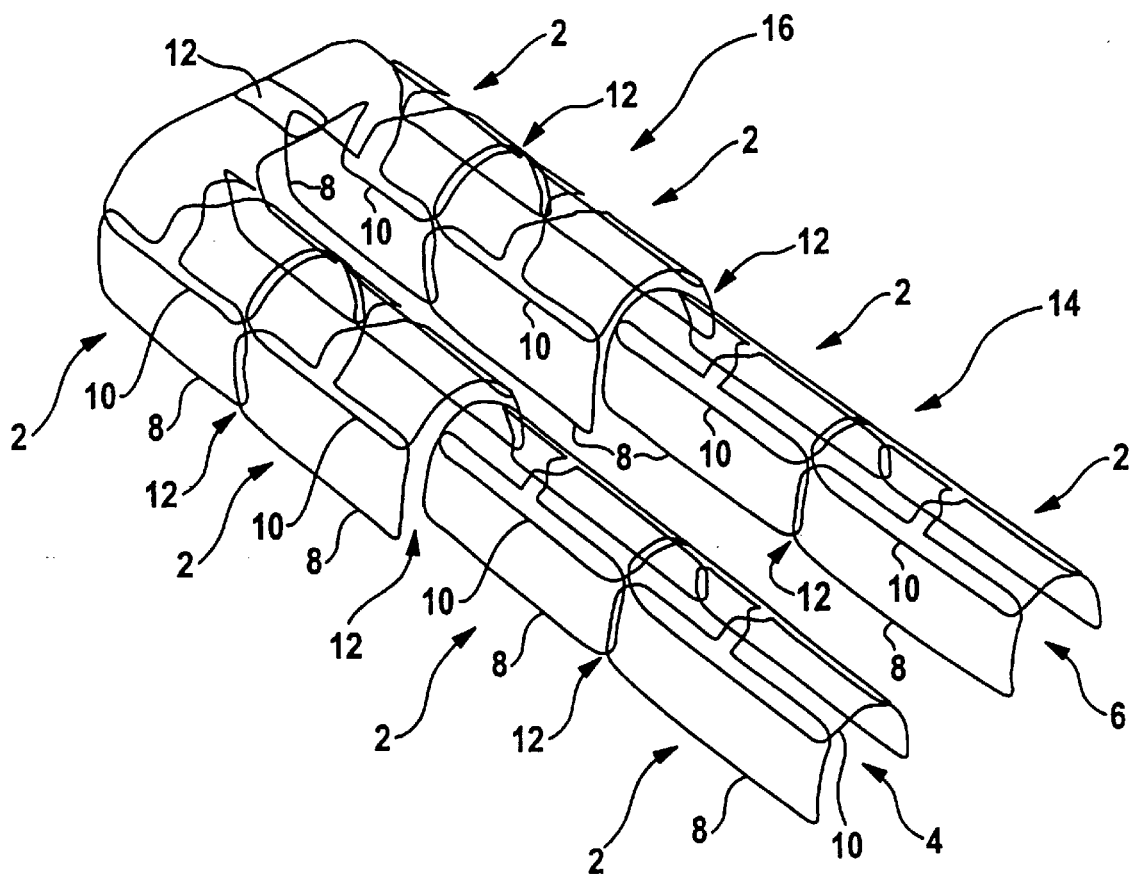
FIG. 1 is a perspective view of the inventive antenna structure of a bilateral antenna array for magnetic resonance examinations of the lower extremities.

The antenna array shown in a perspective view in FIG. 1 is fashioned for magnetic resonance examinations of the lower extremities. With a high image quality, the antenna array enables the continuous display of the blood vessels, without repositioning the patient. The antenna array is formed by of array elements 2 that are decoupled from each other and that are structurally independent, these array elements being arranged in two adjacent rows 4 and 6. During the application, the array elements 2 of each row 4 and 6 enclose the upper areas of a leg and the lateral areas of a leg. In addition, they cover a part of the lower torso of a patient to be examined.

Each array element 2 has two antenna elements 8 and 10 whose respective sensitivity axes reside perpendicular to one another. The antenna elements 8 and 10 of each array element 2 are basically arranged in a plane, with the antenna element 8 being fashioned as a saddle coil pair and the antenna element 10 being fashioned as a ring coil. The decoupling of adjoining antenna elements ensues by geometrical means in the form of an overlap area 12. Further, a decoupling of a known type using pre-amplifiers is used. An input impedance of the preamplifier respectively connected to the antenna elements 8, 10 (not shown in FIG. 1) is matched to the antenna conductors of the antenna elements 8, 10 in a high-resistance manner, so that voltages induced in the antenna elements 8, 10 cannot produce antenna currents. The antenna elements 8 and 10 within the individual array elements 2 are decoupled from each other by their geometrical arrangement. The geometrical decoupling and the pre-amplifier decoupling are described in detail in PCT Application WO89/05115.

The antenna array has a lower area 14 that is provided for the examination of the lower legs, and an upper area 16 that is provided for the examination of the thighs and of the lower torso. The array elements 2 of the lower area 14 are curved more strongly and have a smaller examination space than the array elements 2 of the upper area 16 in order achieve a high filling factor and therewith a high signal-to-noise ratio given the anatomically different outer dimensions. In both areas 14 and 16, the array elements 2 are fashioned in a U-shaped manner.

Figure 2:
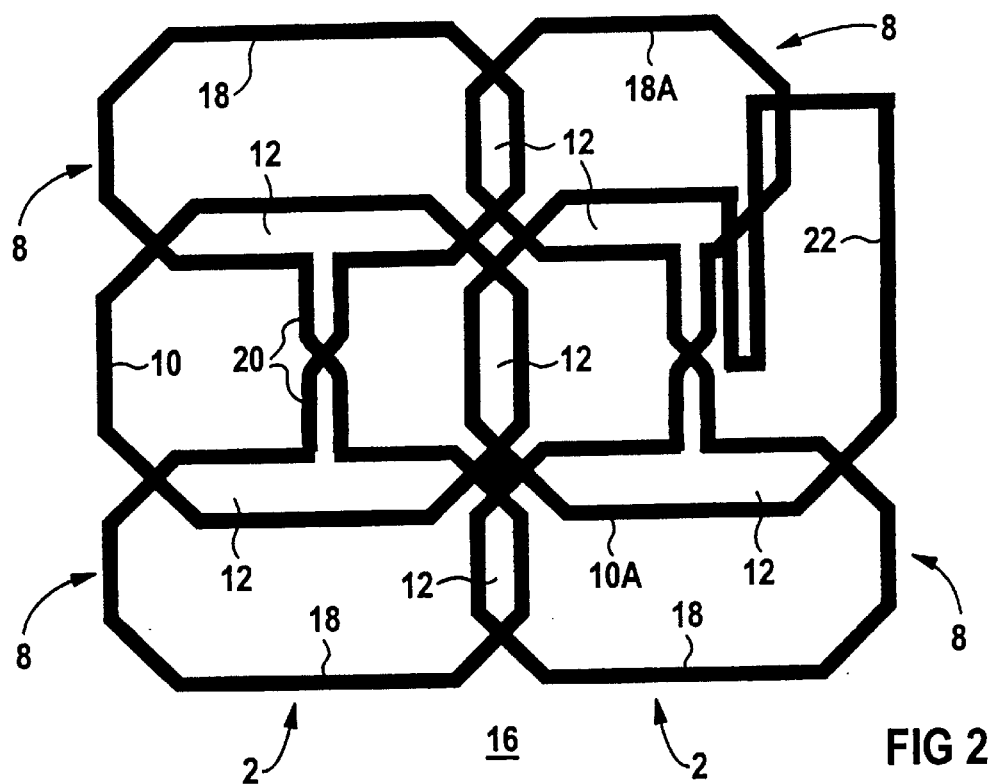
FIG. 2, in a developed view, shows two array elements of the inventive array that are provided as a component of the antenna array for the imaging of the upper area of the extremities.

In a developed view, FIG. 2 shows the two array elements 2 of the upper area 16 in the row 6. The saddle coil pair 8 is formed by two conductor loops 18 that are connected in series via a crossed connection 20. For clarity, capacitors that are required for tuning the conductor loop 18 to the actual frequency of the magnetic resonance device are not shown. For anatomical reasons, the saddle coil pair 8 that images the upper leg area has a somewhat smaller conductor loop 18A, which is positioned at the inside of the upper end of the thigh.

For reasons of anatomy, the upper array element 2 also has a somewhat differently fashioned ring coil 10A than the other array elements 2. The ring coil 10A has a loop-like part 22, which is not curved in a U-shaped manner as the other parts of the array element, but which extends substantially in a plane in the antenna array. This loop-liked part 22 serves the purpose of improving the image representation in the transition from the leg to the lower torso. With the correspondingly mirror-symmetrically fashioned loop-like part of the adjacent row 4, an overlap for the geometrical decoupling is therewith possible, as is also shown in FIG. 1.

Figure 3:
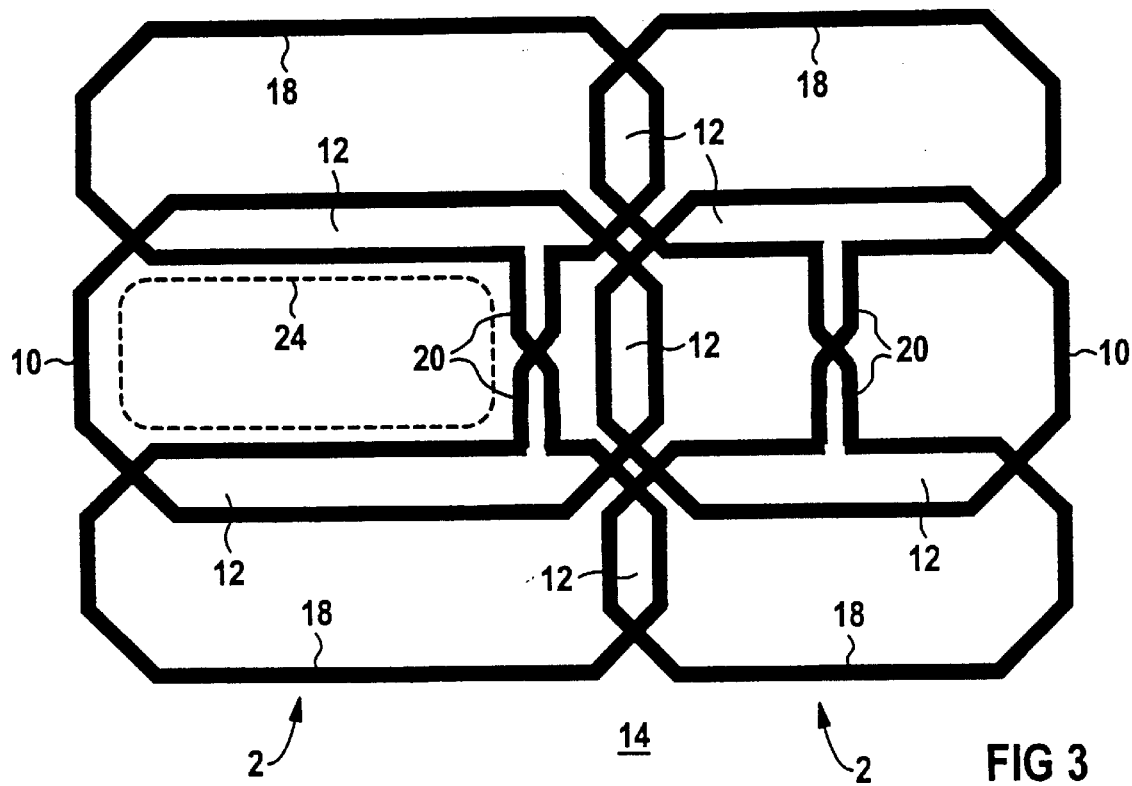
FIG. 3, in a developed view, shows two array elements of the inventive array that are fashioned as a component of the antenna array for the lower areas of the extremities.

In a developed view, FIG. 3 shows the two array elements 2 of the lower area 14. In the lower area 14, the lowest array element—the left array element in FIG. 3—is fashioned longer than the other array elements 2 in the antenna array. Moreover, the crossed connection 20 between the two conductor loops 18 is unsymmetrically arranged. Therewith, space is created for an opening 24 through which parts of the foot can project during the application of the antenna array, allowing the lower part 14 to be tightly placed against the lower legs.

Figure 4:
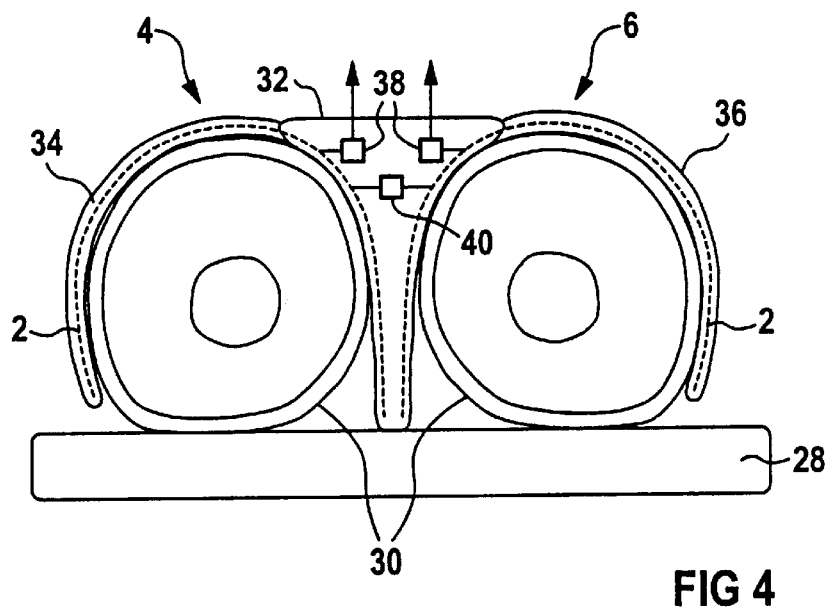
FIG. 4 is a sectional view showing the mechanic construction of the inventive antenna array.

Schematically in a cross section, FIG. 4 shows the structure of the antenna array. The antenna array is fashioned as a cover for a patient bed 28. The lower extremities are referenced 30. The cover is formed by a rigid middle bar 32 and flexible side parts 34 and 36. The array elements 2 each proceed, corresponding to the schematic illustration for the two rows 4 and 6, from the outside of the middle bar 32 via the flexible side parts 34 and 36.

Signal processing circuits 38 are arranged in the middle bar 32; among other things, these signal processing circuits 38 combine the antenna signals of the antenna elements 8 and 10 of each array element 2 in correct phase relation after amplification. Additionally, decoupling circuits 40 that compensate magnetic couplings of the conductor loops 18 of the two rows 4 and 6 adjoining the bar 32 are installed in the middle bar 32. Further, electrical signal connections for the array elements 2 are guided through the bar 32. Circuits for detuning (to activate and deactivate) of the individual array elements 2 are also situated here. This detuning (deactivation) ensues, for example, transiently (dynamically) for employed array elements 2 during the transmission phase in the measuring sequence. Array elements 2 that are not required for a specific measuring can be permanently (statically) untuned during the complete measuring cycle.

Figure 5:
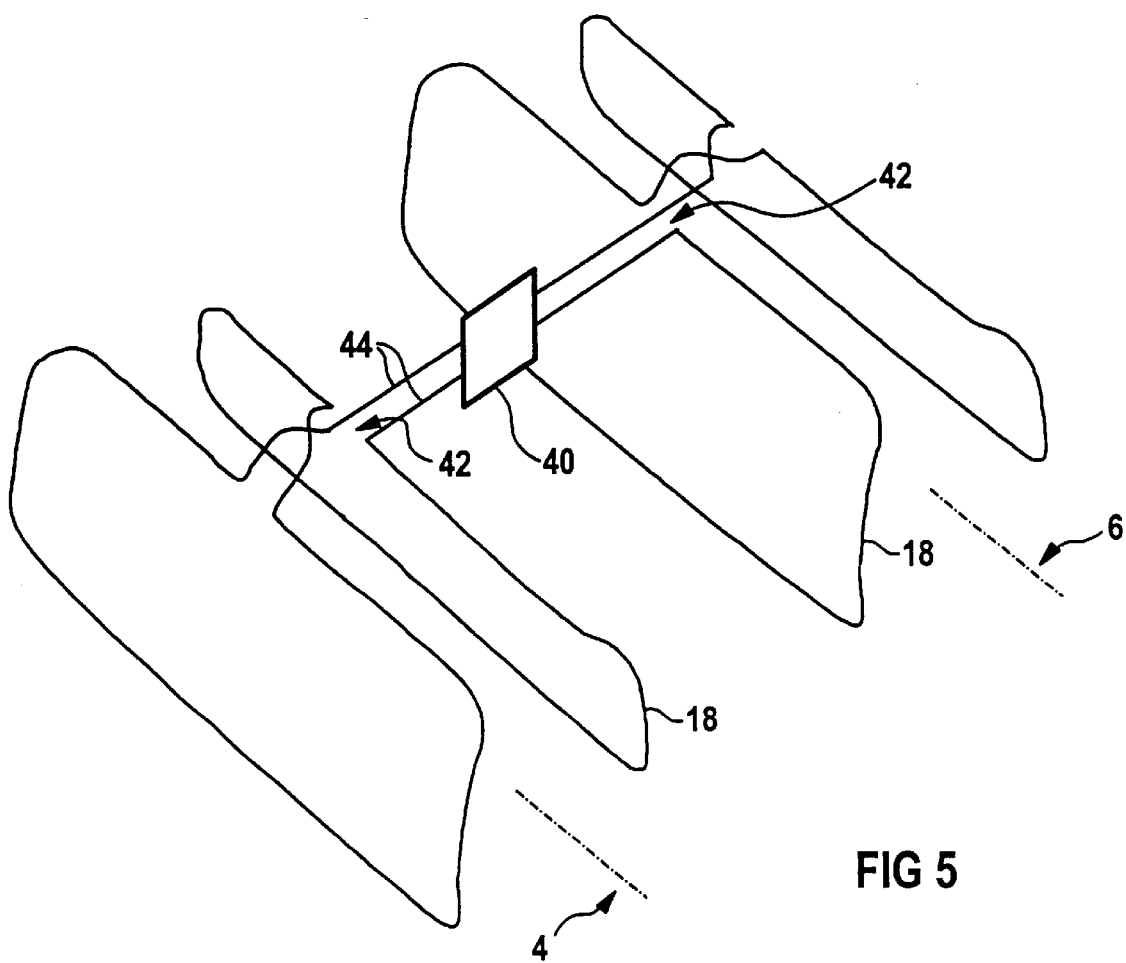
FIG. 5 is a perspective view showing two saddle coil pairs of the inventive array bilaterally arranged with a decoupling circuit.

In a perspective view, FIG. 5 shows the arrangement of the decoupling circuit 40 for two adjoining conductor loops 18 of the two rows 4 and 6. The decoupling circuit 40 is described in detail in U.S. Pat. No. 5,708,361. One interruption 42 is present in the conductors of both saddle coil pairs 8. The two interruptions 42 are connected to one another via conductors 44 and are short-circuited with a capacitor at (not shown); the capacitance of this capacitor can be dimensioned such that magnetic couplings are compensated. In addition, the decoupling circuit 40 also includes circuits for balancing (skin effect wave barriers) in order to prevent coupling via the relatively long connection lines 44.

Figure 6:
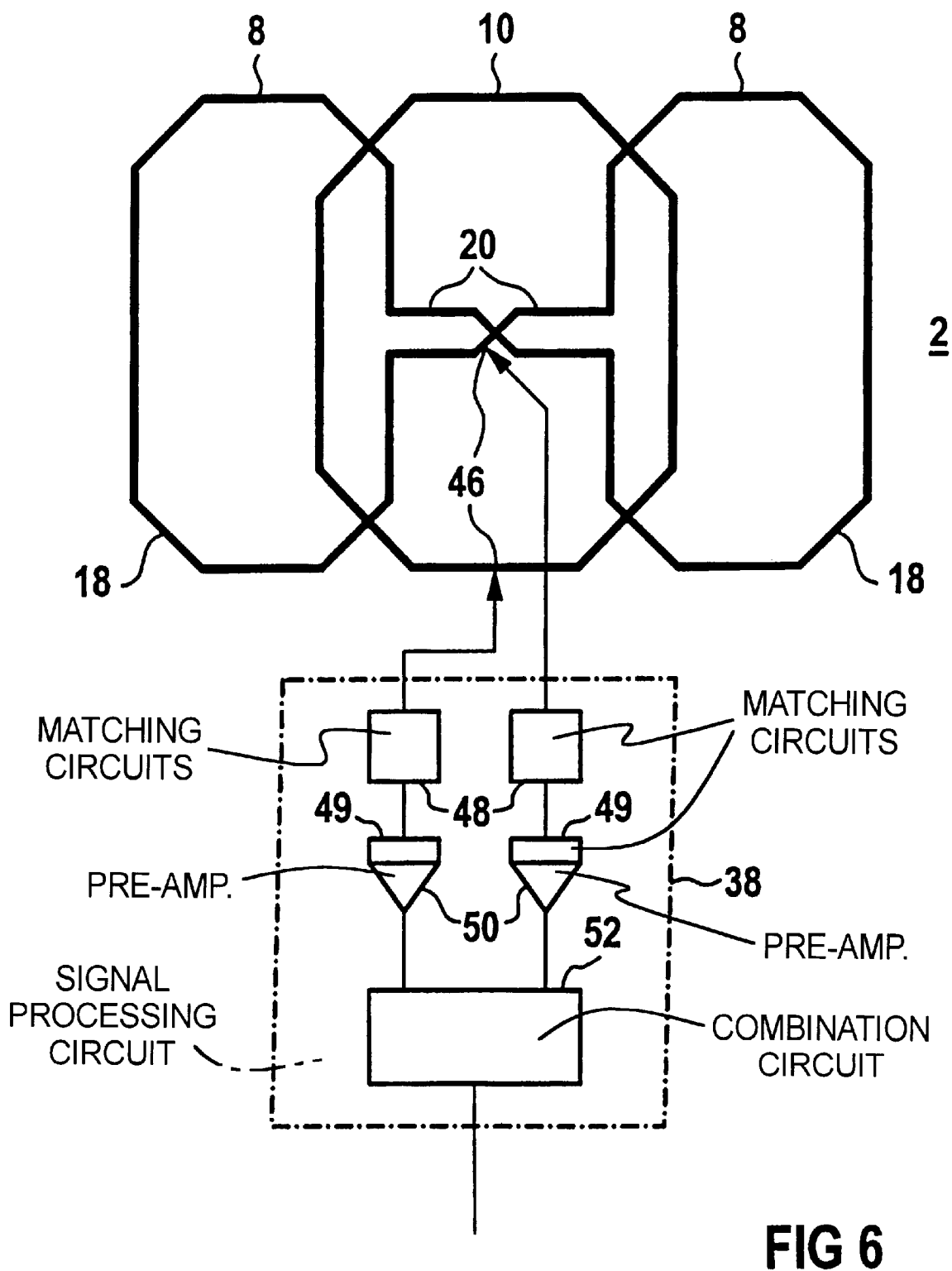
FIG. 6 is a block diagram of a combination circuit connected to an array element of the inventive array.

Representing the remaining array elements 2, FIG. 6 shows the structure of the signal processing circuit 38 for an array element 2. Each antenna element 8, 10 is connected to a matching circuit 48 at a signal connection 46 that is preferably symmetrically arranged relative to the antenna conductors. The matching circuit 48 transforms the antenna impedance, for example, to 50Ω. A further matching circuit 49 that is followed by a pre-amplifier 50 follows each matching circuit 48. The input impedance of the pre-amplifiers 50 is matched to the antenna elements 8,10 in a high-resistance manner by means of the further matching circuit 49 (as explained in PCT Application WO 89/05115). Subsequently, a combination in correct phase relation of the signals received by the antenna elements 8, 10 ensues in a combination circuit 52 that follows the pre-amplifiers 50. Particularly short lines to the pre-amplifiers 50 result due to the arrangement of the signal processing circuit 38 in the middle bar. Therewith, the pre-amplifier input impedance can be matched to the antenna elements 8, 10 in an almost ideally high-resistance manner without line influences that have an attenuating effect. The transformation of the antenna impedance to 50Ω can also be foregone. Then, the input impedance of the pre-amplifier 50 must be correspondingly adapted to the antenna impedance. Then, the matching circuit 48 is foregone.

Although modifications and changes may be suggested by those skilled in the art, it is the intention of the inventor to embody within the patent warranted hereon all changes and modifications as reasonably and properly come within the scope of his contribution to the art.

We claim as our invention:

1. An antenna array for magnetic resonance examinations, comprising a plurality of array elements that are decoupled from each other and that are independent, said array elements being disposed in two adjacent rows each array element comprising two antenna elements with respective sensitivity axes residing perpendicularly to one another, a middle bar disposed between the rows and fastening respective neighboring antenna elements in the rows to each other, and each of the array elements having a flexible portion proceeding from the middle bar in a transverse direction.

2. An antenna array according to claim 1, wherein the antenna elements of a first of said rows neighbor respective antenna elements of a second of said rows and comprising a decoupling circuit connecting the respective antenna elements in said first and second rows.

3. An antenna array according to claim 1 comprising assigned process circuits connecting the antenna elements to one another.

4. An antenna array according to claim 1 wherein each of said array elements comprises a saddle coil pair and a ring coil.

5. An antenna array according to claim 4, wherein the array elements disposed are opposite each other in the rows.

6. An antenna array according to claim 1 wherein the array elements of each row are curved in the same direction.

7. An antenna array according to claim 6, wherein the array elements of each row are curved in a U-shaped manner.

8. An antenna array according to claim 6 wherein a first group of the array elements is more strongly curved and surrounds a smaller examination space than a second group of the array elements (2).

9. An antenna array according to claim 1 wherein each of the array elements has a flexible portion.

10. An antenna array according to claim 1 comprising a single pre-amplifier in the middle bar connected to the antenna elements.

11. An antenna array according to claim 1 comprising a single matching circuit connected to the antenna elements, said matching circuit transforming an input impedance of said pre-amplifier to the antenna elements in a high-resistance manner.

12. An antenna array according to claim 1, wherein the array elements form a cover with an open bottom for a patient bed.

13. An antenna array according to claim 1, wherein the antenna elements of a first of said rows neighbor respective antenna elements of a second of said rows and comprising a decoupling circuit connecting the respective antenna elements in said first and second rows, said decoupling circuit comprising skin effect wave barriers.

* * * * *